United States Patent

De Vecchi

[11] Patent Number: 6,119,958
[45] Date of Patent: Sep. 19, 2000

[54] CASE PARTICULARLY FOR DEODORANTS, INSECTICIDES, MOTH-REPELLANT WITH A SNAP OPENING AND CLOSING MECHANISM

[75] Inventor: Monna De Vecchi, Porza, Switzerland

[73] Assignee: Beta Pictoris Inc., Monrovia, Liberia

[21] Appl. No.: 09/291,875

[22] Filed: Apr. 14, 1999

[30] Foreign Application Priority Data

May 4, 1998 [IT] Italy .................................. MI980310 U

[51] Int. Cl.[7] .......................................................... A61L 9/04
[52] U.S. Cl. ................................................................ 239/55
[58] Field of Search .................................... 239/53, 54, 55, 239/56, 57, 58, 59; 220/366.1, 348, 785, 787, 203.23, 345.2, 345.3, 345.4

[56] References Cited

U.S. PATENT DOCUMENTS

| | | | |
|---|---|---|---|
| 2,531,737 | 11/1950 | Lyon, Jr. | 220/348 |
| 3,976,246 | 8/1976 | Hauri et al. | 239/57 |
| 4,702,372 | 10/1987 | Ackeret | 220/348 |

*Primary Examiner*—Andres Kashnikow
*Assistant Examiner*—Christopher S. Kim
*Attorney, Agent, or Firm*—Notaro & Michalos P.C.

[57] ABSTRACT

A case for deodorants and the like is equipped with a snap opening and closing mechanism. The case has a base for the product, a guide cylinder that is integral with the base for a sliding cover, and a spring to act of the cover to carry it from a closing position to an opening position. Locks capable of engaging this cover when the latter is respectively in the opening and/or closing position are also provided. A clearing button is capable of disengaging this cover from on of the locks to carry it from a closing position to an opening position.

2 Claims, 2 Drawing Sheets

CASE PARTICULARLY FOR DEODORANTS, INSECTICIDES, MOTH-REPELLANT WITH A SNAP OPENING AND CLOSING MECHANISM

FIELD AND BACKGROUND OF THE INVENTION

This invention proposes a case provided particularly for deodorants, both paste and granulated deodorants, for insecticides, moth-repellant, perfumed essences or other room perfumes, provided with a snap opening and closing mechanism which allows the case to be in a closing position for carrying, where the release and dispersion of the perfume in the room are prevented, to an opening position where a port opens allowing the fragrance to come out.

In particular the case according to the invention is characterized by the shape of the snap mechanism which allows the opening and closing of the case with one hand, in a quick and simple way. This offers a remarkable practicality, particularly appreciable when the case is positioned in places that are accessible with difficulty.

More particularly the case mechanism according to the invention allows to control the opening of the case simply by pressing a push button and to close it by pressing on the cover of the case.

Room deodorants are known, for example deodorants for the house, deodorants for the car, etc., wherein the perfumed essence is mixed or incorporated into a support consisting for example of a paste, granules or the like, which reduces the perfume diffusion, guaranteeing thereby a controlled release and a duration in time of the deodorant effect.

Many of these foresee a sealing wrap provided with a bored part closed by an adhesive sheet or the like. By removing this sheet, the deodorant is allowed to come out from the wrap and diffuse in the room.

This solution however causes the inconvenience that once the wrapping is opened, it is no more possible to close it again, therefore the deodorant continues to come out until its total consumption.

Cases are also known provided with a cap which can be partially unscrewed, opening thereby a port allowing in this way the perfume emission; the cases can be closed by screwing again the cover.

This solution is however not very practical, since it requires the engagement of both the hands to open and close the case, which consequently is inappropriate for example to be used in the car or to be positioned in places accessible with difficulty to the end to be hidden from view, for example on a cupboard, etc.

The Italian application for utility model no. MI96U 0155 of Mar. 1, 1996 filed by the applicant here describes a case for deodorants with a pressure opening, comprising a base containing the deodorant material, a hollow rod integral with said base, the base being provided internally with ribs which end downwardly with a double dentel, a piston sliding into said rod, elastic means capable to push upwardly said piston, a pawl mounted with the possibility to rotate on this rod and provided internally with ribbings capable to be inserted into the seats between a couple of ribs integral with said rod, these ribs being capable to engage the ribs of the base rod to enable the cover to move only in axial translation, a toothing provided downwardly with respect to the cover rod capable to engage the upper edge of these ribbings to give partial rotations to the pawl when the cover is pressed, wherein this toothing is staggered with respect to said ribbings so as to give at every cover operation a rotation to the pawl equal to the width of only one of the two dentels.

This device enables to open and close the case using only one hand, with the inconvenience, however, of a rather complex shape and therefore with a remarkable constructive complication, ever since the unit consists of different pieces, for each of which it is necessary to provide a mould having a complex shape and therefore very expensive.

Even the assembly results rather complex and, owing to the presence of different movable parts which have to rotate, there is also the risk of jammings.

SUMMARY OF THE INVENTION

This invention inserts now in this field with the scope to improve the present cases and propose a case consisting of only three parts, subject to the action of a spring, executing only one movement of axial translation with a consequent greater simplicity and safety of operation.

BRIEF DESCRIPTION OF THE DRAWINGS

This invention will now be described in detail, by way of a not limitative example, with reference to the enclosed drawings, wherein:

With reference to FIG. 1, the case comprises a base 1, which has a perimeter with a substantially cylindrical wall 2 and a cover from which projects a shell 4, having a shape complementary to the one of the wall 2 of the base and designed to be inserted around the base.

DESCRIPTION OF THE PREFERRED EMBODIMENT

The base is designed to contain the deodorant product. Inside the base, with the central zone, there are an outer cylindrical body 5, a inner cylindrical body 6 acting as guide means as well as two couples of tabs 7 and 8, which shall be better described afterwards.

Figure 3:
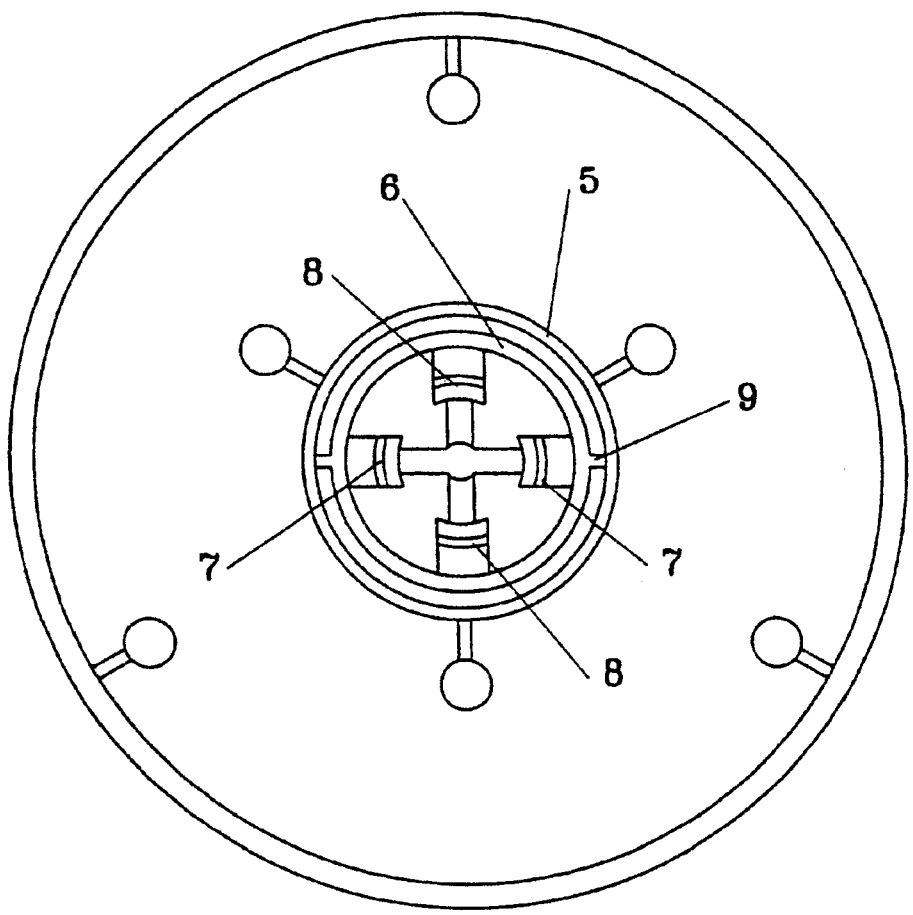
FIG. 3 is a top view of the base with the cover removed.

One or more connection walls, indicated with reference 9 in FIG. 3, connect the outer and inner cylindrical bodies, 5 and 6 of the base to each other.

The cylindrical bodies 5 and 6 act as a guide for the cover 3, which is provided, always at the central part, with a downwardly projecting cylindrical body or guide 10 apt to be inserted into the space between the bodies 5 and 6 of the base.

In the cylindrical body 10 there are one or more notches, not shown in figure, in correspondence with the walls 9. This shape serves to secure the exact positioning of the cover as regards the base.

Figures 1, 1A:
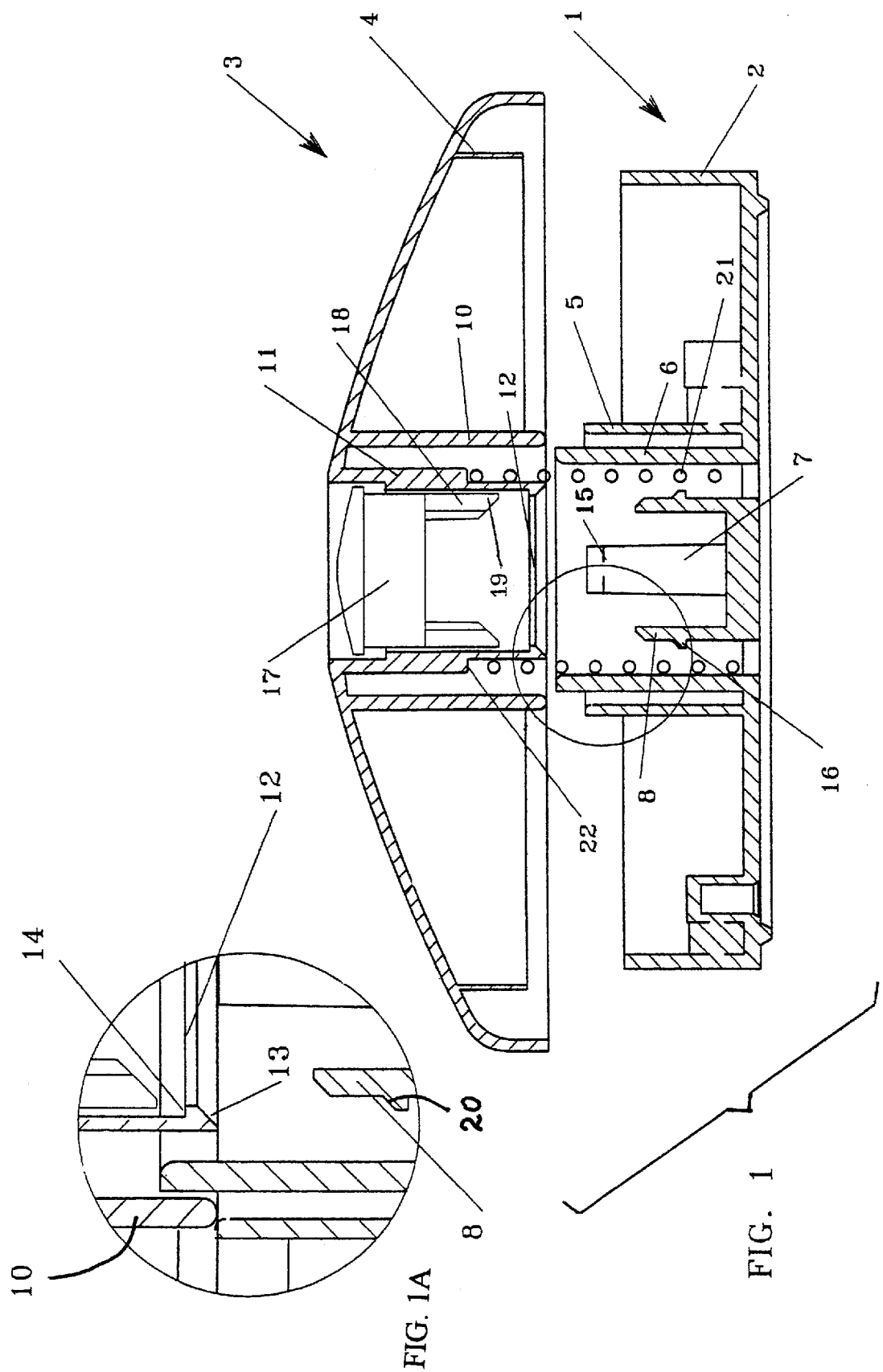
FIG. 1 shows, in cross-section, a case according to the invention, with the cover and the base separated.
FIG. 1A is a detail from the circled area of FIG. 1
Figure 2:
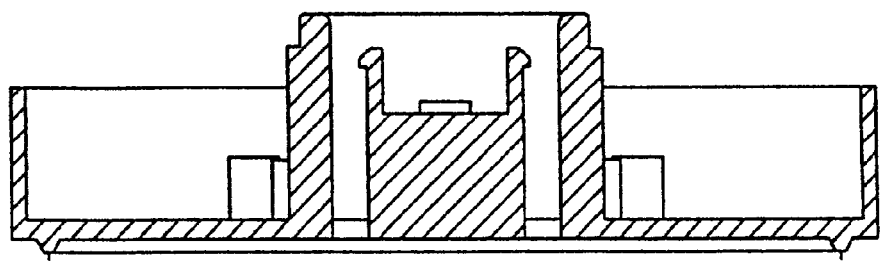
FIG. 2 is the cross-section of the base according to a plane orthogonal to the plane of FIG. 1.

Inside the cylindrical body 10 of the cover there is a second cylindrical body 11, which lower edge has an annular relief 12, which has the lower wall 13 inclined downwardly and outwardly and the upper wall 14 substantially flat (these details are better visible in the FIG. 1A of FIG. 1).

The annular relief 12 is designed to engage the tabs 7 and 8 to lock the cover respectively in the opening and closing positions.

To this end, dentels, indicated respectively with references 15 and 16, are provided on the couples of the tabs 7 and 8.

These dentels are at different heights and particularly the dentels 15 are positioned at the upper ends of the longer tabs, while the dentels 16 are provided on the shorter tabs, at an appropriate height.

The dentels both 15 and 16 have the lower wall substantially horizontal, while the upper wall is inclined, with the same inclination of the wall 13 of the annular relief 12.

It is finally provided inside the cylinder 11 of the cover, a push button 17 which can slide inside said cylindrical body and has, downwardly, a couple of tabs 18, which lower wall, indicated with reference 19, is inclined downwardly and outwardly.

The tabs 18 correspond, as regard the position, with the tabs 8 in the base, the tabs 8 having an upper edge 20 with the same inclination as the walls 19 of the push button.

Inside the cylindrical body 6 is then inserted a helicoidal spring 21, which presses against a step 22 provided in the upper cylindrical body 11 to push the cover upwardly in the opening position.

The operation takes place as follows.

Once the product is put into the case consisting of the base 2, the spring 21 is placed into its seat and the whole is closed by inserting the cover.

During the insertion, the cylindrical body 10 is inserted into the space between the cylindrical bodies 5 and 6 of the base to guide the cover in its travel.

By pressing the cover downwardly, the inclined wall 13 of the annular relief 12 on the cylindrical body 11 engages the inclined surface of the dentels 15 on the longer tabs 7, which are caused to bend inwardly to be opened by a snap afterwards when the relief 13 overcame the dentels 15. The engagement between the flat surfaces of the dentels 15 and the upper surface 14 of the relief 12 constitutes a stop which prevents the cover from being removed.

This position corresponds with the opening position of the case, with the cover remaining slightly raised, pushed by the spring 21. By pressing still downwardly the cover 3, the inclined wall 13 of the annular relief 12 engages this time the dentels 13 provided on the shorter tabs 8.

Also these tabs are elastically deformed bending inwardly and enabling the relief 12 to overcome the dentels 16, which lower wall, substantially flat, engages then the wall 14 of the annular relief 12 to lock the cover in the closing position.

To open the cover, the push button 17 is operated by pressing it downwardly.

The inclined walls 19 of the tabs 18 interact now with the inclined upper edge 20 of the tabs 8 by pressing them inwardly till to disengage the tabs 16 from the relief 12 and enabling thereby the cover to go up, pushed by the spring 21.

The cover goes then in the opening position with the relief 12 engaging the dentels 15 of the longer tabs 7.

To close the cover it is therefore sufficient to press with the hand thereonto, while the opening takes place through the push button 17. Within the said idea of solution, any change of detail can be then provided.

For example different couples of tabs can be provided, the shape of the case or the different bodies 5 and 6, 10 and 18 can be different from the cylindrical one, without going out from the protection sphere of this invention.

Also the sizes as well as the material employed can vary depending on the employ needs.

What is claimed is:

1. A case for a deodorant product, comprising:

a base (1) for the product;

a sliding cover over the base, the cover having a guide (10);

guide means (5, 6) in said base for engaging the guide (10) of said sliding cover;

biasing means (21) acting on said cover to bias said cover from a closed position to an open position with respect to said base;

locking means (12, 15, 16) for holding said cover in said closed and said open positions; and clearing means (17, 19) for disengaging said locking means to allow said cover to move from the closed position to the open position due to the bias of said biasing means;

said cover including a cylindrical body (11) extending downwardly and having an annular edge (12) with a lower inclined wall (13);

said locking means comprising flexible tabs (7, 8) provided integrally with said base, each tab having a dentel (15, 16) for engaging said annular edge (12) when the cover is respectively in the closed and open positions, said dentels having upper inclined surfaces, lower surfaces of said dentels and an upper surface (14) of said annular edge being substantially flat; and said biasing means comprising elastic means (21) for acting on said cover to push the cover to the open position, said clearing means (17, 19) acting on one of said tabs (8) for disengaging said dentels of said one of said tabs from said annular edge.

2. A basic according to claim 1 wherein said clearing means comprises a push button (17) in said cylindrical body of said cover, said push button having a lower end with further tabs (18) in a position aligned with the one of said tabs (8) for disengaging the dentels of said one of said tabs from the annular edge when the push button is pushed down in the cover, said further tabs (18) having lower ends with inclined surfaces (19) for acting on corresponding inclined surfaces provided on the upper edge of said one of said tabs in said base so that when said push button is pushed down, said inclined surface (19) of said further tabs (18) bend said one of said tabs (8) to disengage said dentels of said one of said tabs from said annular edge.

* * * * *